United States Patent [19]

Cragoe, Jr. et al.

[11] 4,208,413

[45] Jun. 17, 1980

[54] N-PYRAZINECARBONYL-N'-ALKOXYCARBONYL AND N',N''-BIS(ALKOXYCARBONYL)GUANIDINES AND PROCESSES FOR PREPARING SAME

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 966,532

[22] Filed: Dec. 4, 1978

Related U.S. Application Data

[63] Continuation-in-part of Ser. No. 774,359, Mar. 4, 1977, abandoned.

[51] Int. Cl.$^2$ ............................................. A61K 31/495
[52] U.S. Cl. ..................................... 424/250; 544/405; 544/407
[58] Field of Search ......................... 544/407; 424/250

[56] References Cited

U.S. PATENT DOCUMENTS

| 2,542,856 | 2/1951 | Wright, Jr. .......................... 548/138 |
| 3,240,780 | 3/1966 | Cragoe, Jr. et al. .................. 544/407 |
| 3,274,191 | 9/1966 | Cragoe, Jr. et al. .................. 544/407 |
| 3,313,813 | 4/1967 | Cragoe, Jr. .......................... 544/407 |
| 3,328,404 | 6/1967 | Pollak et al. ........................ 544/407 |
| 3,573,305 | 3/1971 | Cragoe, Jr. et al. .................. 544/405 |
| 3,833,578 | 9/1974 | Ambrogi et al. ..................... 544/407 |
| 4,085,211 | 4/1978 | Cragoe, Jr. et al. .................. 544/407 |
| 4,115,573 | 9/1978 | Cragoe, Jr. et al. .................. 544/407 |

Primary Examiner—Donald G. Daus
Assistant Examiner—James H. Turnipseed
Attorney, Agent, or Firm—Michael C. Sudol, Jr.; Harry E. Westlake, Jr.

[57] ABSTRACT

The case involves novel N-pyrazinecarbonyl-N'-alkoxycarbonyl and N',N''-bis(alkoxycarbonyl)guanidines and processes for preparing same. The compounds are excellent eukalemic agents possessing diuretic and natriuretic properties.

8 Claims, No Drawings

N-PYRAZINECARBONYL-N'-ALKOXYCARBONYL AND N',N"-BIS(ALKOXYCARBONYL)GUANIDINES AND PROCESSES FOR PREPARING SAME

RELATED CASES

This case is a continuation-in-part of U.S. Ser. No. 774,359 filed Mar. 4, 1977, now abandoned.

BACKGROUND OF THE INVENTION

The background to this invention U.S. Pat. No. 3,313,813 patented Apr. 11, 1967 and issued to Edward J. Cragoe, Jr., shows novel (3-amimo-5,6-disubstituted-pyrazinoyl)guanidine compounds. The compounds of the U.S. Pat. No. 3,313,813 are useful because they possess diuretic and natriuretic properties. They differe from most of the known, effective diuretic agents, however, in that the compounds of the U.S. Pat. No. 3,313,813 selectively enhance the excretion of sodium ions while simultaneously causing a decrease in excretion of potassium ions. The potassium loss, which is caused by known diuretics, often results in a severe muscular weakness. Since the compounds of the U.S. Pat. No. 3,313,813 prevent the potassium depletion, they have this decided advantage as diuretics. As diuretic agents, they can be used for the treatment of edema, hypertension and other diseases or conditions known to be responsive to this therapy and are especially useful when used in combination with or concomitantly with potassium losing diuretic agents.

Applicants' instant compounds shown in Formula I subsequently differ from the compounds shown in U.S. Pat. No. 3,313,813, in that they have a different group in place of the guanidino group of the compounds in the stated U.S. Patent. Applicants have found that the N'-alkoxycarbonylguanidine and N', N"-bis(alkoxycarbonyl) guanidino groups change the pharmaceutical action and utility of these compounds. It has been found in U.S. Pat. No. 3,313,813 that the pyrazinoylguanidine compounds therein described when co-administered with other diuretic agents known to enhance the elimination of potassium ions along with sodium ions, will maintain the potassium ion excretion at approximately the normal or control rate and thus overcome this undesirable property of other diuretic agents.

In actuality, applicants' compounds in the instant case as further described, accomplish the objective previously achieved by using a combination of the pyrazinoylguanidine compounds of the U.S. Pat. No. 3,313,813 with diuretic agents which cause elimination of sodium with concomitant excessive potassium elimination. Thus, the effect of introducing alkoxycarbonyl groups to the pyrazinoylguanidine compounds of the U.S. Pat. No. 3,313,813 results in producing eukalemic saluretic agents. Since the compounds of the instant invention are thus eukalemic saluretic agents they constitute single entities which are useful for the treatment of edema and hypertension and other diseases or conditions known to be responsive to this therapy.

SUMMARY OF THE INVENTION

The instant case covers novel-N-pyrazinecarbonyl-N'-alkoxycarbonyl and N',N"-bis(alkoxycarbonyl)-guanidines and processes for making the same. The novel compounds of this invention are depicted in Formulae I and II below.

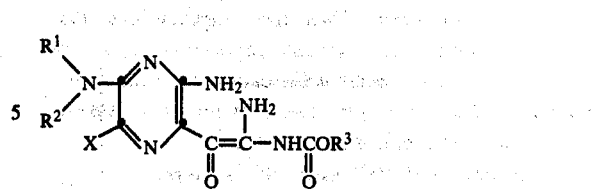

Formula I and

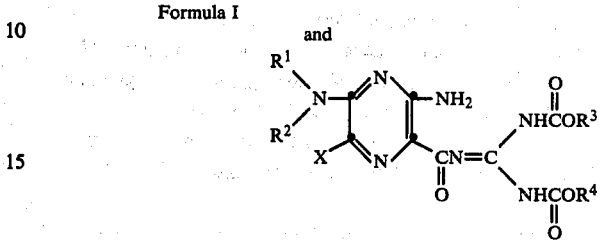

Formula II wherein $R^1$ is hydrogen, lower alkyl having from 1 to 5 carbon atoms such as methyl, ethyl, isopropyl, n-butyl, n-pentyl, cycloalkyl having from 3 to 6 carbon atoms such as cyclopropyl, cyclopentyl and cyclohexyl;

lower alkenyl having from 2 to 3 carbon atoms such as allyl;

$R^2$ is hydrogen, lower alkyl having from 1 to 5 carbon atoms such as methyl, ethyl, isopropyl and n-pentyl, $R^1$ and $R^2$ can be joined to form with the nitrogen atom to which they are attached, a heterocyclic ring having 3 to 6 carbon atoms therein;

$R^3$ and $R^4$ are lower alkyl having from 1 to 5 carbon atoms such as methyl, ethyl, isopropyl, butyl and pentyl, cycloalkyl having from 3 to 6 nuclear carbon atoms such as cyclopropyl, cyclopentyl and cyclohexyl, alkenyl, having from 2 to 5 carbon atoms such as allyl, aralkyl wherein the alkyl portion had from 1 to 3 carbon atoms such as benzyl and alkoxyalkyl wherein the alkyl portions have 1 to 5 carbon atoms such as ethoxy methoyl;

X is halo, such as fluoro, chloro, bromo or iodo; and
the pharmaceutically acceptable non-toxic acid addition salts thereof.

The preferred compounds of this invention, in other words, those having enhanced diuretic, saluretic activity while maintaining unchanged potassium blood levels are those compounds of Formulae I and II wherein $R^1$ and $R^2$ are hydrogen, $R^3$ and $R^4$ are lower alkyl having 1 to 3 carbon atoms;

X is chloro, and the pharmaceutically acceptable non-toxic acid addition salts thereof.

The compounds of this invention as shown by Formulae I and II and the preferred compounds discussed above are useful because they possess diuretic and natriuretic properties. In addition, they are useful eukalemic saluretics, in other words, the compounds of the instant case cause neither loss or abnormal retention of potassium ions. In contradistinction, the pyrazinoylguanidine compounds of U.S. Pat. No. 3,313,813 do cause a decrease in the excretion of potassium ions. However, other well known diuretics such as furosemide, chlorthalidone and acetazolamide cause an increase in potassium excretion which often results in muscular weakness. Applicants' compounds combine in a single agent the advantages of a combination of the known pyrazinylguanidine diuretics of U.S. Pat. No. 3,313,813 which decrease potassium with the known diuretics which cause a potassium loss. Thus, the compounds of this invention maintain the excretion of potassium at approximately normal levels while causing an increased renal elimination of sodium ions and water which is the desirable characteristic of the diuretic.

Also covered within the scope of the above Formulae I and II compounds and the preferred compounds are the pharmaceutically acceptable acid addition salts thereof. These salts can be made by reacting the free base with a pharmaceutically acceptable acid such as for example, hydrochloric acid, sulfuric acid, hydrobromic acid or isethionic acid. These salts, as stated above, are to be considered as included in this invention.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds disclosed in this invention in Formulae I and II and the preferred compounds can be formed according to the process described below,

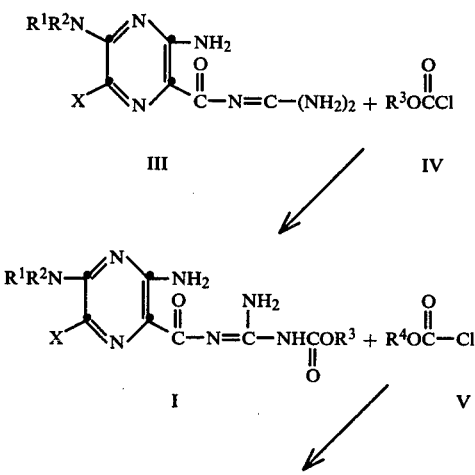

-continued

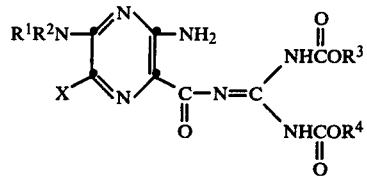

II involving a reaction of a pyrazinoylguanidine (III) with an ester of chloroformic acid chloride (IV) to produce the desired product (I). (Some of the original starting material (III) is also produced as the hydrochloride salt.) The product of Formula I may then be treated with the same or different ester of chloroformic acid chloride (V) to produce the desired product (II). The reaction is usually run in an inert solvent preferably a solvent such as tetrahydrofuran, dioxane, dimethoxyethane, pyridine or acetonitrile at a temperature from about room temperature to the reflux temperature of the particular solvent used. The reaction time is usually from one to 48 hours and the reactants are in mole to mole ratios. None of these reaction conditions are critical and they can be vaired by those skilled in the art.

All the starting materials used in the process described above are shown in and disclosed in U.S. Pat. No. 3,313,813 mentioned previously or at least can be obviously prepared from compounds disclosed in the aforementioned patent.

Representative examples to illustrate this invention are the following:

EXAMPLE 1

3,5-Diamino-6-chloro-N-[(ethoxycarbonylamino)iminomethyl]-2-pyrazinecarboxamide hemihydrate To a stirred suspension of N-amidino-3,5-diamino-6-chloro-2-pyrazinecarboxamide (4.6 g., 0.02 mole) in pyridine (50 ml.) cooled to 15° C. is added ethyl chloroformate (1 ml.) during a 3 minute period. The reaction is stirred at 25° for ¾ of an hour, filtered and heated with water (200 ml.) to give 1.0 g. of 3,5-diamino-6-chloro-N-[(ethoxycarbonylaminio)iminomethyl]-2-pyrazinecarboxamide hemihydrate which melts at 188° C. after recrystallization from ethanol.

Elemental analysis for $C_9H_{12}CLIV_7O_3$ (.½ $H_2O$);
Calc.: C, 34.79; H, 4.22; Cl, 11.41.
Found: C, 34.37; H, 4.12; Cl, 11.44.

EXAMPLE 2

3,5-Diamino-6-chloro-N-[bis(ethoxycarbonylamino)-methylene]-2-pyrazinecarboxamide To a stirred suspension of N-amidino-3,5-diamino-6-chloro-2-pyrazinecarboxamide (27.6 g., 0.12 mole) in pyridine (300 ml.) is added ethyl chloroformate (12.0 ml., 0.15 mole) during a 5 minute period. The reaction is stirred at 25° for 2 hours during which time the starting material dissolves and the hydrochloride of the starting material precipitates. The latter is filtered from the reaction and discarded. The filtrate is treated with water (700 ml.) to give 16 g. (71%) of 3,5-diamino-6-chloro-N-[bis(ethoxycarbonylamino)methylene]-2-pyrazinecarboxamide which melts at 213° C. after recrystallization from ethanol.

Analysis for $C_{12}H_{16}ClN_7O_5$

Calc.: C, 38.56; H, 4.31; N, 26.23.
Found: C, 38.50; H, 4.43; N, 26.16.

EXAMPLE 3

By following substantially the procedure described in Example 2 but substituting for the N-amidino-3,5-diamino-6-chloro-2-pyrazinecarboxamide therein described an equimolar amount of the compounds shown in List 1 below there is obtained an equivalent amount of the compounds shown in List 2 below.

List 1
N-amidino-3-amino-5-methylamino-6-chloro-2-pyrazinecarboxamide;
N-amidino-3-amino-5-ethylamino-6-chloro-2-pyrazinecarboxamide;
N-amidino-3-amino-5-propylamino-6-chloro-2-pyrazinecarboxamide;
N-amidino-3-amino-5-isopropylamino-6-chloro-2-pyrazinecarboxamide;
N-amidino-3-amino-5-butylamino-6-chloro-2-pyrazinecarboxamide;
N-amidino-3-amino-5-cyclopropylamino-6-chloro-2-pyrazinecarboxamide;
N-amidino-3-amino-5-cyclopentylamino-6-chloro-2-pyrazinecarboxamide;
N-amidino-3-amino-5-allylamino-6-chloro-2-pyrazinecarboxamide;
N-amidino-3-amino-5-dimethylamino-6-chloro-2-pyrazinecarboxamide;
N-amidino-3-amino-5-diethylamino-6-chloro-2-pyrazinecarboxamide;
N-amidino-3-amino-5-pyrrolidino-6-chloro-2-pyrazinecarboxamide;
N-amidino-3-amino-5-piperidino-6-chloro-2-pyrazinecarboxamide.

List 2
3-amino-5-methylamino-6-chloro-N-[bis(ethoxycarbonylamino)-methylene]-2-pyrazinecarboxamide;
3-amino-5-ethylamino-6-chloro-N-[bis(ethoxycarbonylamino)-methylene]-2-pyrazinecarboxamide;
3-amino-5-propylamino-6-chloro-N-[bis(ethoxycarbonylamino)-methylene]-2-pyrazinecarboxamide;
3-amino-5-isopropylamino-6-chloro-N-[bis(ethoxycarbonylamino)-methylene]-2-pyrazinecarboxamide;
3-amino-5-butylamino-6-chloro-N-[bis(ethoxycarbonylamino)-methylene]-2-pyrazinecarboxamide;
3-amino-5-cyclopropylamino-6-chloro-N-[bis(ethoxycarbonylamino)-methylene]-2-pyrazinecarboxamide;
3-amino-5-cyclopentylamino-6-chloro-N-[bis(ethoxycarbonylamino)-methylene]-2-pyrazinecarboxamide;
3-amino-5-allylamino-6-chloro-N-[bis(ethoxycarbonylamino)-methylene]-2-pyrazinecarboxamide;
3-amino-5-dimethylamino-6-chloro-N-[bis(ethoxycarbonylamino)-methylene]-2-pyrazinecarboxamide;
3-amino-5-diethylamino-6-chloro-N-[bis(ethoxycarbonylamino)-methylene]-2-pyrazinecarboxamide;
3-amino-5-pyrrolidino-6-chloro-N-[bis(ethoxycarbonylamino)-methylene]-2-pyrazinecarboxamide;
3-amino-5-piperidino-6-chloro-N-[bis(ethoxycarbonylamino)-methylene]-2-pyrazinecarboxamide;

EXAMPLE 4

By following procedures of Example 1 but substituting for the N-amidino-3,5-diamino-6-chloro-2-pyrazinecarboxamide therein described an equimolar amount of compounds in Example 3, List 1, there is obtained
3-amino-5-methylamino-6-chloro-N-[(ethoxycarbonylamino)iminomethyl]-2-pyrazinecarboxamide;
3-amino-5-ethylamino-6-chloro-N-[(ethoxycarbonylamino)iminomethyl]-2-pyrazinecarboxamide;
3-amino-5-propylamino-6-chloro-N-[(ethoxycarbonylamino)iminomethyl]-2-pyrazinecarboxamide;
3-amino-5-isopropylamino-6-chloro-N-[(ethoxycarbonylamino)iminomethyl]-2-pyrazinecarboxamide;
3-amino-5-butylamino-6-chloro-N-[(ethoxycarbonylamino)iminomethyl]-2-pyrazinecarboxamide;
3-amino-5-cyclopropylamino-6-chloro-N-[(ethoxycarbonylamino)iminomethyl]-2-pyrazinecarboxamide;
3-amino-5-cyclopentylamino-6-chloro-N-[(ethoxycarbonylamino)iminomethyl]-2-pyrazinecarboxamide;
3-amino-5-allylamino-6-chloro-N-[(ethoxycarbonylamino)iminomethyl]-2-pyrazinecarboxamide;
3-amino-5-dimethylamino-6-chloro-N-[(ethoxycarbonylamino)iminomethyl]-2-pyrazinecarboxamide;
3-amino-5-diethylamino-6-chloro-N-[(ethoxycarbonylamino)iminomethyl]-2-pyrazinecarboxamide;
3-amino-5-pyrrolidino-6-chloro-N-[(ethoxycarbonylamino)iminomethyl]-2-pyrazinecarboxamide;
3-amino-5-piperidino-6-chloro-N-[(ethoxycarbonylamino)iminomethyl]-2-pyrazinecarboxamide;

EXAMPLE 5

By following substantially the procedure described in Example 2 but substituting for the N-amidino-3,5-diamino-6-chloro-2-pyrazinecarboxamide therein described an equimolar amount of the compounds shown in List 1 below there is obtained an equimolar amount of the compounds shown in List 2 below.

List 1
N-amidino-3,5-diamino-6-fluoro-2-pyrazinecarboxamide;
N-amidino-3,5-diamino-6-bromo-2-pyrazinecarboxamide;
N-amidino-3,5-diamino-6-iodo-2-pyrazinecarboxamide.

List 2
3,5-diamino-6-fluoro-N-[bis(ethoxycarbonylamino)methylene]-2-pyrazinecarboxamide;
3,5-diamino-6-bromo-N-[bis(ethoxycarbonylamino)methylene]-2-pyrazinecarboxamide;
3,5-diamino-6-iodo-N-[bis(ethoxycarbonylamino)methylene]-2-pyrazinecarboxamide.

EXAMPLE 6

By following substantially the procedure described in Example 2 but substituting for the ethylchloroformate therein described an equimolar amount of the compounds shown in List 1 below there is obtained an equimolar amount of the compounds shown in List 2 below.

List 1
methyl chloroformate;
propyl chloroformate;
isopropyl chloroformate;
butyl chloroformate;
cyclopentyl chloroformate;
cyclohexyl chloroformate.

List 2
3,5-diamino-6-chloro-N-[bis(methoxycarbonylamino)-methylene]-2-pyrazinecarboxamide;
3,5-diamino-6-chloro-N-[bis(propoxycarbonylamino)-methylene]-2-pyrazinecarboxamide;
3,5-diamino-6-chloro-N-[bis(isopropoxycarbonylamino)-methylene]-2-pyrazinecarboxamide;

3,5-diamino-6-chloro-N-[bis(butoxycarbonylamino)me-
thylene]-2-pyrazinecarboxamide;
3,5-diamino-6-chloro-N-[bis(cyclopentyloxycar-
bonylamino)-methylene]-2-pyrazinecarboxamide;
3,5-diamino-6-chloro-N-[bis(cyclohexyloxycar-
bonylamino)-methylene]-2-pyrazinecarboxamide.

EXAMPLE 7

By following substantially the procedure described in Example 1 but substituting for the N-amidino-3,5-diamino-6-chloro-2-pyrazinecarboxamide therein described an equimolar amount of the compounds shown in List 1 below there is obtained an equimolar amount of the compounds shown in List 2 below.

List 1
N-amidino-3,5-diamino-6-fluoro-2-pyrazinecarboxa-
mide;
N-amidino-3,5-diamino-6-bromo-2-pyrazinecarboxa-
mide;
N-amidino-3,5-diamino-6-iodo-2-pyrazinecarboxamide.
List 2
3,5-diamino-6-fluoro-N-[(ethoxycar-
bonylamino)iminomethyl]-2-pyrazinecarboxamide;
3,5-diamino-6-bromo-N-[(ethoxycar-
bonylamino)iminomethyl]-2-pyrazinecarboxamide;
3,5-diamino-6-iodo-N-[(ethoxycar-
bonylamino)iminomethyl]-2-pyrazinecarboxamide.

EXAMPLE 8

By following substantially the procedure described in Example 2 but substituting for the ethylchloroformate therein described an equimolar amount of the compounds shown in List 1 below there is obtained an equimolar amount of the compounds shown in List 2 below.

List 1
methyl chloroformate;
propyl chloroformate;
isopropyl chloroformate;
butyl chloroformate;
cyclopentyl chloroformate;
cyclohexyl chloroformate.
List 2
3,5-diamino-6-chloro-N-[(methoxycar-
bonylamino)iminomethyl]-2-pyrazinecarboxamide;
3,5-diamino-6-chloro-N-[(propoxycar-
bonylamino)iminomethyl]-2-pyrazinecarboxamide;
3,5-diamino-6-chloro-N-[(isopropoxycar-
bonylamino)iminomethyl]-2-pyrazinecarboxamide;
3,5-diamino-6-chloro-N-[(butoxycar-
bonylamino)iminomethyl]-2-pyrazinecarboxamide;
3,5-diamino-6-chloro-N-[(cyclopentyloxycar-
bonylamino)iminomethyl]-2-pyrazinecarboxamide;
3,5-diamino-6-chloro-N-[(cyclohexyloxycar-
bonylamino)iminomethyl]-2-pyrazinecarboxamide.

EXAMPLE 9

3,5-Dimino-6-chloro-N-[(ethoxycarbonylamino)(me-
thoxycarbonylamino)methylene]-2-pyrazinecarboxa-
mide To a stirred suspension of 3,5-diamino-6-chloro-N-[(ethoxycarbonylamino)iminomethyl]-2-pyrazinecarboxamide hemihydrate (3.11 g., 0.01 mole) in pyridine (25 ml.) is added methyl chloroformate (0.5 ml). The reaction mixture is stirred at 25° C. for 2 hours, filtered and heated with water (50 ml.) to give 3,5-diamino-6-chloro-N-[(ethoxycarbonylamino)(methoxycarbonylamino)methylene]-2-pyrazinecarboxamide.

What is claimed is:
1. A compound of the formula:

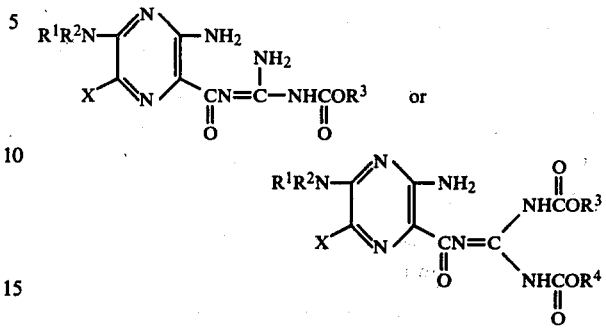

wherein
$R^1$ is hydrogen, lower alkyl having from 1 to 5 carbon atoms, cycloalkyl having from 3 to 6 carbon atoms, lower alkenyl having from 2 to 3 carbon atoms;
$R^2$ is hydrogen, lower alkyl having 1 to 5 carbon atoms;
$R^1$ and $R^2$ can be joined to form with the nitrogen atom to which they are attached a heterocyclic ring having 3 to 6 carbon atoms therein;
$R^3$ and $R^4$ are lower alkyl having from 1 to 5 carbon atoms;
cycloalkyl having from 3 to 6 nuclear carbon atoms, alkenyl having 2 to 5 carbon atoms, aralkyl wherein the alkyl portion has 1 to 3 carbon atoms and alkoxyalkyl wherein the alkyl portions have 1 to 5 carbon atoms;
X is halogen; and the pharmaceutically acceptable non-toxic acid addition salts thereof.
2. A compound of the formula;

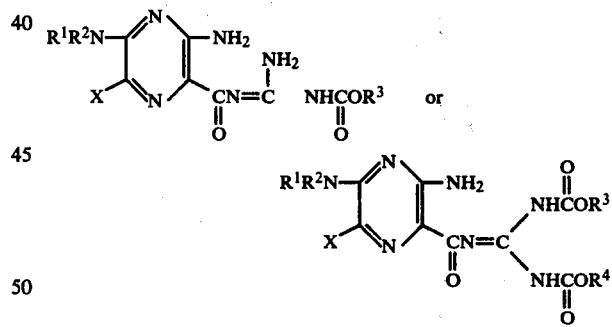

wherein
$R^1$ and $R^2$ are hydrogen;
$R^3$ and $R^4$ are lower alkyl having from 1 to 3 carbon atoms;
X is chloro; and the pharmaceutically acceptable non-toxic acid addition salts thereof.
3. A compound of claim 2 wherein
$R^1$ and $R^2$ are hydrogen;
$R^3$ is ethyl;
X is chloro; which is 3,5-diamino-6-chloro-N-[(ethoxycarbonylamino)-iminomethyl]-2-pyrazinecarboxamide.
4. A compound of claim 2 wherein
$R^1$ and $R^2$ are hydrogen;
$R^3$ and $R^4$ are ethyl;

X is chloro; which is 3,5-diamino-6-chloro-N-[bis(ethoxycarbonylamino)-methylene-2-pyrazinecarboxamide.

5. A method of treating edema and/or hypertension which comprises administering to a patient a pharmacologically acceptable dose of a compound of the formula;

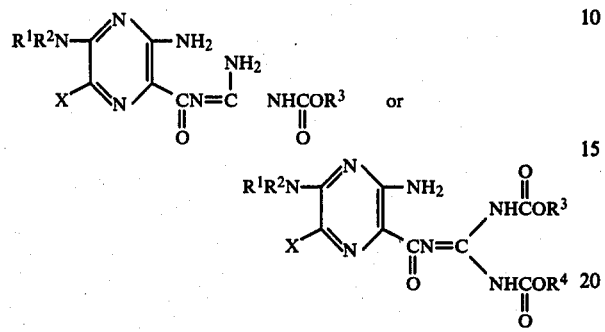

wherein
R¹ is hydrogen;
lower alkyl having from 1 to 5 carbon atoms, cycloalkyl having from 3 to 6 carbon atoms, lower alkenyl having from 2 to 3 carbon atoms;
R² is hydrogen,
lower alkyl having 1 to 5 carbon atoms;
R¹ and R² can be joined to form with the nitrogen atom to which they are attached a heterocyclic ring having 3 to 6 carbon atoms therein;
R³ and R⁴ are lower alkyl having from 1 to 5 carbon atoms;
cycloalkyl having from 3 to 6 nuclear carbon atoms, alkenyl having 2 to 5 carbon atoms, aralkyl wherein the alkyl portion has 1 to 3 carbon atoms and alkoxyalkyl wherein the alkyl portions have 1 to 5 carbon atoms;
X is halogen; and the pharmaceutically acceptable non-toxic acid addition salts thereof.

6. A method of treating edema and hypertension which consists essentially of administering to a patient in need of such treatment a unit dosage of from 5 mg. to 1 gm./day of the compound of the formula:

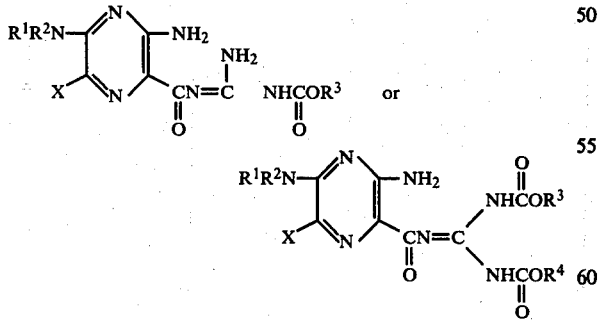

wherein
R¹ and R² are hydrogen;
R³ and R⁴ are lower alkyl having from 1 to 3 carbon atoms;
X is chloro; and the pharmaceutically acceptable non-toxic acid addition salts thereof.

7. A pharmaceutical composition comprising as an active ingredient a compound of the formula:

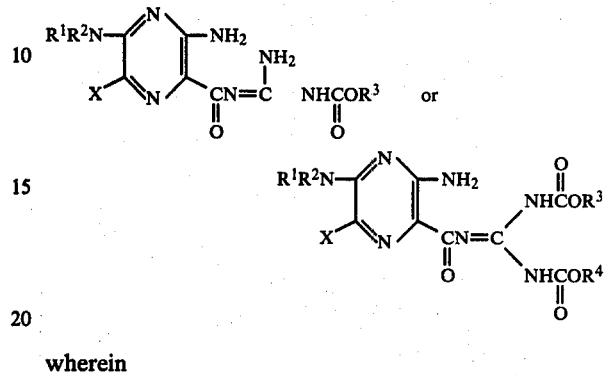

wherein
R¹ is hydrogen,
lower alkyl having from 1 to 5 carbon atoms,
cycloalkyl having from 3 to 6 carbon atoms, lower alkenyl having from 2 to 3 carbon atoms;
R² is hydrogen,
lower alkyl having 1 to 5 carbon atoms;
R¹ and R² can be joined to form with the nitrogen atom to which they are attached a heterocyclic ring having 3 to 6 carbon atoms therein;
R³ and R⁴ are lower alkyl having from 1 to 5 carbon atoms;
cycloalkyl having from 3 to 6 nuclear carbon atoms, alkenyl having 2 to 5 carbon atoms, aralkyl wherein the alkyl portion has 1 to 3 carbon atoms and alkoxyalkyl wherein the alkyl portions have 1 to 5 carbon atoms;
X is halogen; and the pharmaceutically acceptable non-toxic acid addition salts thereof.

8. A pharmaceutical composition consisting essentially of an active ingredient of a compound of the formula;

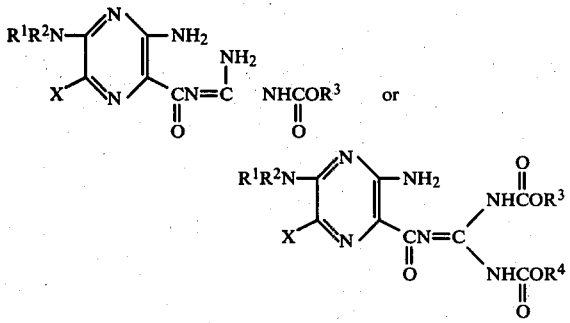

wherein
R¹ and R² are hydrogen
R³ and R⁴ are lower alkyl having from 1 to 3 carbon atoms;
X is chloro; and the pharmaceutically acceptable non-toxic acid addition salts thereof.

* * * * *